United States Patent [19]

Elloy et al.

[11] Patent Number: 5,314,480
[45] Date of Patent: May 24, 1994

[54] PATELLAR COMPONENTS

[75] Inventors: Martin A. Elloy, North Yorkshire; Robert Johnson, Hoylake, both of Great Britain

[73] Assignee: DePuy International Ltd., Leeds, United Kingdom

[21] Appl. No.: 828,861

[22] PCT Filed: Jun. 4, 1990

[86] PCT No.: PCT/GB90/00860
  § 371 Date: Jan. 31, 1992
  § 102(e) Date: Jan. 31, 1992

[87] PCT Pub. No.: WO91/15168
  PCT Pub. Date: Oct. 17, 1991

[30] Foreign Application Priority Data
  Jun. 2, 1989 [GB] United Kingdom ............... 8912684

[51] Int. Cl.[5] .................................................. A61F 2/38
[52] U.S. Cl. ........................................ 623/20; 623/16; 623/18
[58] Field of Search ........................... 623/16, 18, 20

[56] References Cited

U.S. PATENT DOCUMENTS

| | | | |
|---|---|---|---|
| 3,878,566 | 4/1975 | Bechtol | 623/20 |
| 3,927,423 | 12/1975 | Swanson | 623/20 |
| 4,007,495 | 2/1977 | Frazier | 623/20 |
| 4,285,070 | 8/1981 | Averill | 623/20 |
| 5,019,104 | 5/1991 | Whiteside et al. | 623/20 |

FOREIGN PATENT DOCUMENTS

| | | | |
|---|---|---|---|
| 0307654 | 3/1989 | European Pat. Off. | 623/20 |
| 0327297 | 8/1989 | European Pat. Off. | 623/20 |
| 3332354 | 3/1985 | Fed. Rep. of Germany | 623/20 |
| 2594323 | 2/1986 | France | 623/20 |
| 2615096 | 11/1988 | France | 623/20 |
| 2625096 | 6/1989 | France | 623/20 |
| 2009601 | 6/1979 | United Kingdom | 623/20 |
| 9115168 | 10/1991 | World Int. Prop. O. | 623/20 |

Primary Examiner—David Isabella
Assistant Examiner—Debra S. Brittingham
Attorney, Agent, or Firm—Merchant, Gould, Smith, Edell, Welter & Schmidt

[57] ABSTRACT

A patellar component 91) for use in conjunction with a prosthetic knee joint of the type comprising a femoral component and a tibial component comprises a metal disc (2) embedded within an ultra-high molecular weight polyethylene disc (3). The polyethylene disc completely surrounds the edge of the metal disc such that the metal disc is flush with the polyethylene disc on one surface of the component. The metal disc may be provided with a knurl or serrations (20) which key into the polyethylene disc to prevent rotation of the two discs. The component (1) is fixed to the patella by means of a central peg (4) and a number of spikes (10).

11 Claims, 5 Drawing Sheets

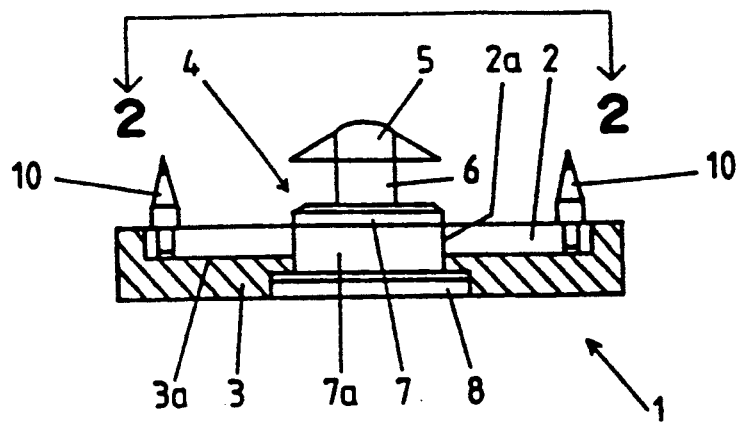
FIG. 1
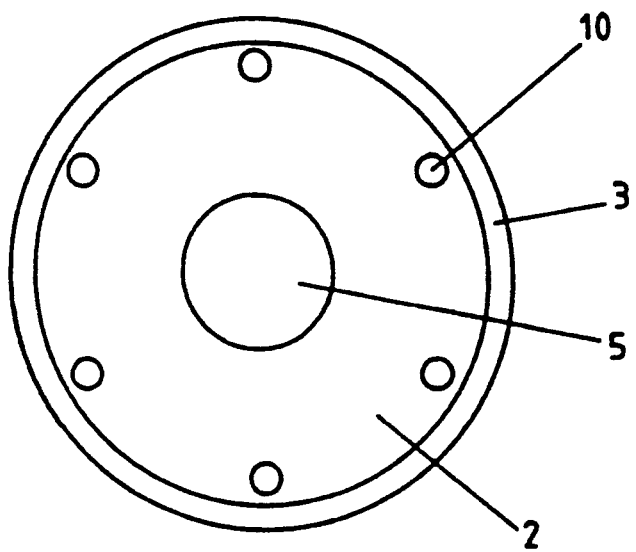
FIG. 2
FIG. 3  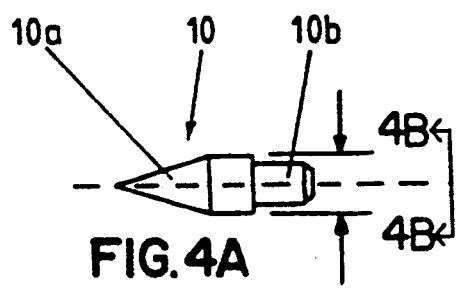 
FIG. 4A    FIG. 4B

PATELLAR COMPONENTS

The present invention relates to an improved metal-backed patellar component for implantation in a patient during a total knee replacement operation.

Recent studies suggest that existing designs of metal backed patellar components lead to failures occurring in which the component is not only destroyed but can also cause other problems such as severe pain, abrasion of the femoral component, metal induced synovitis and severe inflammation.

Such conventional designs commonly comprise a metal base plate embedded within a dome of polyethylene, and these failures have been attributed to one or both of two factors. One factor is the cracking of the polyethylene over the sharp edge of the rectangular cross-section of the metal plate, and the other factor is a shearing dislocation either of the polyethylene from the metal base plate or the shearing of the entire patellar component, including the metal base plate, from the anchoring pegs which remain firmly embedded in the cancellous bone of the natural patella.

It is therefore the aim of the present invention to provide an improved patellar component which eliminates or at least reduces the above-mentioned disadvantages.

According to a first aspect of the present invention there is provided a patellar component for use in conjunction with a prosthetic knee joint of the type which comprises a femoral component and a tibial component, the patellar component comprising a first member having a substantially flat bearing surface for bearing against the femoral component, a second member having means for fixing said second member to the natural patella, and means for holding said first and second members together.

Preferably, the first member is manufactured from a plastics material such as ultra-high molecular weight polyethylene, and the second member is manufactured from metal such as stainless steel.

Conveniently, both first and second members take the form of flat discs, one of which (the first member) has a recess in one surface thereof for receiving the other disc (the second member).

Preferably, the first and second members each have a central aperture therein for receiving a central peg which serves to retain the two members together.

Conveniently, said central peg also includes a fixation device to be driven into the bone of the natural patella.

In addition to the central peg, further means for fixing the second member to the natural patella comprises a series of spikes spaced equally around the circumference of the second member. These spikes are also preferably of metal, and may be separate from or continuous with the second member.

According to a second aspect of the present invention, there is provided an endoprosthetic assembly of components for use in total knee replacement, the assembly including a femoral component for attachment to the femur, a tibial component for attachment to the tibia and patellar component for attachment to the natural patella, in which the patellar component is formed with a substantially flat bearing surface and the femoral component is formed with a substantially cylindrical bearing counterface, the flat surface of the patellar component bearing against the cylindrical surface of the femoral component.

The bearing interengagement between the flat patellar component and the cylindrical counterface on the femoral component of the knee prosthesis guarantees line bearing contact between the patellar and femoral components. Contact stress is reduced in comparison to domed or other contoured patellar components which conventionally run in tracks on the femoral component. With these conventional designs, a combination of variable track geometry, practical manufacturing tolerances and practical surgical inaccuracies may result in there being only point contact between the bearing surfaces of the patellar and femoral components. By way of contrast with the flat patellar component of the present invention, proper tracking and line bearing contact is independent of surgical inaccuracy. The cylindrical patellar bearing surface of the femoral component can be manufactured to extremes of accuracy and surface finish, thus providing an optimum counterface to the patellar component.

An embodiment of the present invention will now be described, by way of example only, with reference to the accompanying drawings in which:

FIG. 1 is a cross-section through a patellar component in accordance with the present invention;

FIG. 2 is a view on line A—A of FIG. 1;

FIG. 3 is a side view of one of the anchoring spikes forming part of the patellar component;

FIG. 4 is a view on line B—B of FIG. 3;

Figure 6:
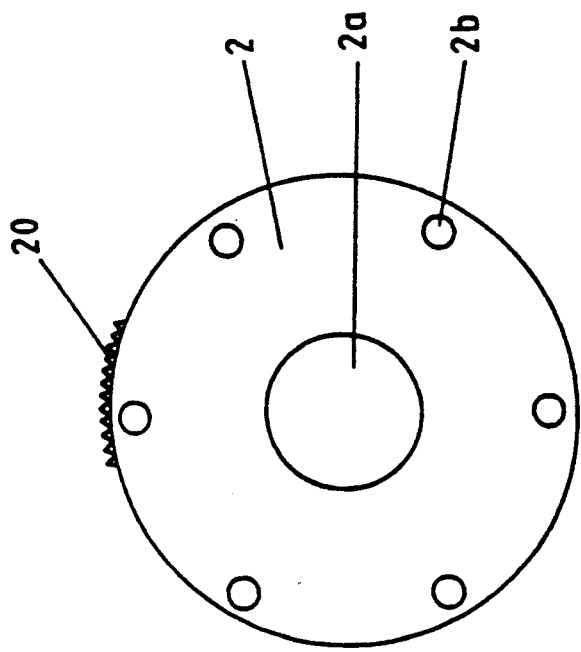
FIG. 6 is a view on line C—C of FIG. 5.
Figure 5:
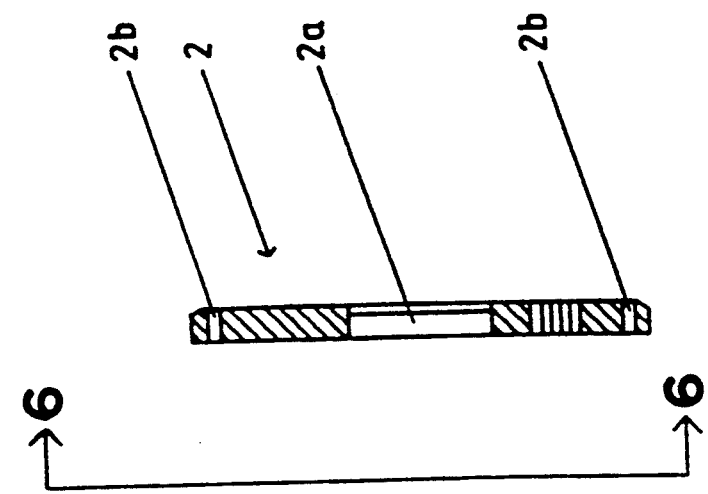
FIG. 5 is a cross-section through the metal base plate forming part of the patellar component.
Figure 8:
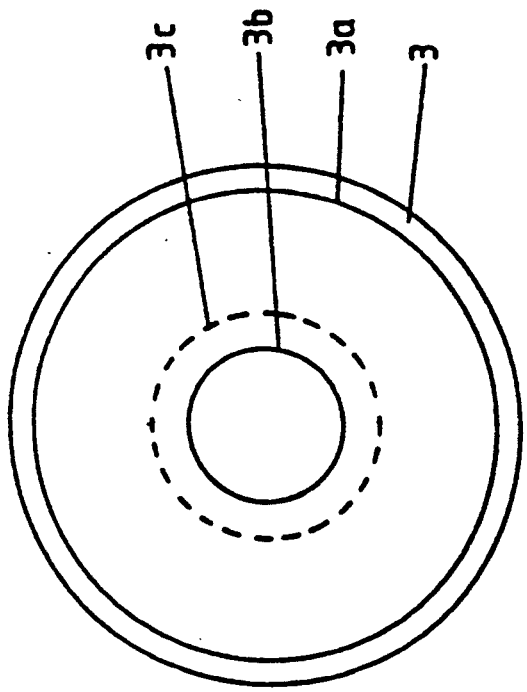
FIG. 8 is a view on line D—D of FIG. 7.
Figure 7:
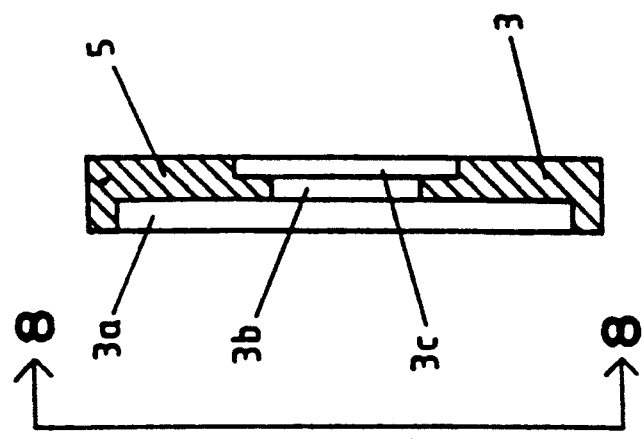
FIG. 7 is a cross-section through the polyethylene disc forming part of the patellar component.
Figure 10:
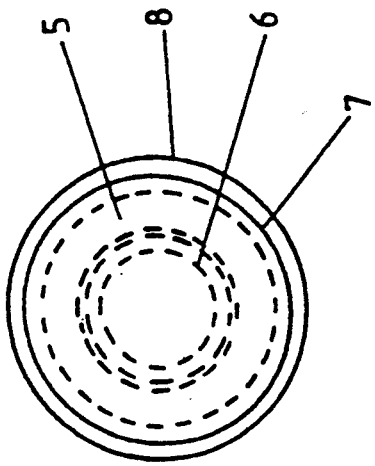
FIG. 10 is a view on line E—E of FIG. 9.
Figure 9:
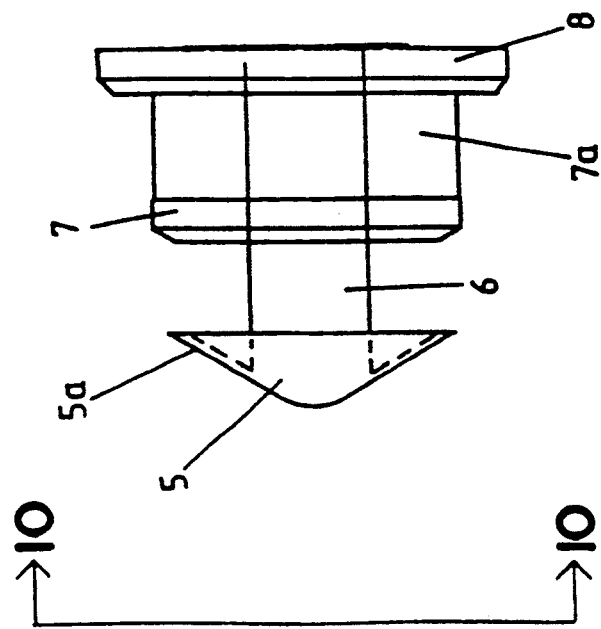
FIG. 9 is a side view of the central peg forming part of the patellar component.

Referring to FIGS. 1-10 the drawings, a patellar component 1 comprises a metal disc 2 embedded within a ultra-high molecular weight polyethylene disc 3. The polyethylene disc 3 is of larger diameter than the metal disc 2 so as to completely surround the edge of the metal disc 2 such that the metal disc 2 is flush with the polyethylene disc on one surface of the component. However, it is not necessary for the metal disc 2 to be flush with the polyethylene disc 3, provided it is located and supported in a shear mode.

To prevent rotation of the polyethylene disc 3 on the metal disc 2, the metal disc 2 is provided with a knurl or serrations 20 which key into the plastic. It should be appreciated that other, different interlocking features are possible.

Alternatively, the serrations or other interlocking features could be omitted to allow the polyethylene disc 3 to rotate relative to the metal disc 2, as this freedom to rotate could impart advantages particularly if contouring of the patella/femoral bearing surfaces is employed.

The metal disc 2 is constructed such as to comprise a tight fit within cavity 3a of polyethylene disc 3, but it is also secured to the polyethylene disc 3 by means of a central peg 4. This peg 4 has a head portion 5 including a flange 5a, a neck portion 6 which leads from the head portion 5 to a first shoulder portion 7. Adjacent the first shoulder portion 7 is a shank portion 7a the diameter of which is slightly less than that of shoulder 7 and the same as the diameter of the central hole 2a in the metal plate. On assembly, the shoulder 7 is forced through hole 2a and re-expands to produce a snap fit. Adjacent shank portion 7a is a second shoulder portion 8 of larger diameter than all of the other portions.

When the central peg is inserted through holes 3a, 3b and 3c in the polyethylene disc and through the hole 2a in the metal disc 2, the second shoulder 8 locates in hole 3a whilst the shank 7a locates in hole 3b and also in hole 2a in the metal disc 2. The first shoulder 7 locates against the edge of hole 2a in metal disc 2.

The head portion 5 of the central peg serves to fix the component temporarily into position in the cancellous bone of the patella, but a more secure fixation is achieved by the provision of a number (six in the illustrated example) of spikes 10 which are equally spaced around the circumference of the component. Each spike 10 has a head portion 10a which is driven into the cancellous bone of the patella, and a neck portion 10b which is an interence fit within hole 2b in the metal disc 2. The spikes 10 are designed to resist shear movement between the implant and the bone. The spikes must have a sufficiently long parallel portion to provide the necessary shear resistance.

The outer surface of polyethylene disc 3 is flat rather than domed, this flat surface bearing against the femoral component. The purpose of the flat profile is to reduce shear stresses induced within the patellar component and at the bone-implant interface. Whereas domed (interlocking) bearing faces result in a shear component in the bearing reaction forces, flat (non-interlocking) surfaces only generate shear forces corresponding to friction which is much lower.

An additional benefit of the flat profile is that the resultant thickness of the disc 3 at the edge of the metal disc 2 is greater than in the conventional designs incorporating a domed polyethylene component. This leads to much greater resistance to cracking of the polythene at the edge of the metal disc, and in addition the central peg reduces the risk of the polyethylene disc 3 shearing off the metal disc 2.

Figure 12:
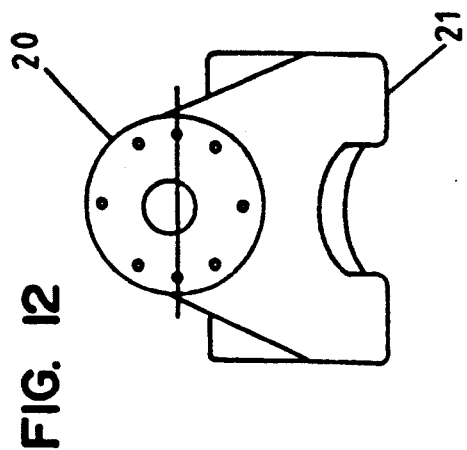
FIGS. 11-13 illustrate use of the patellar component.
Figure 14:
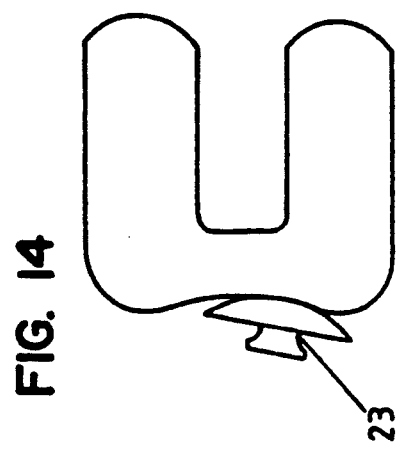
FIG. 14 illustrates a prior art arrangement.
Figure 11:
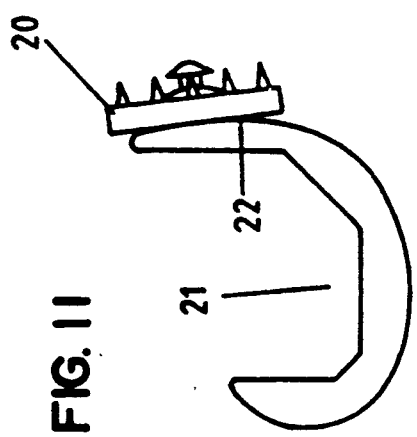
Figure 13:
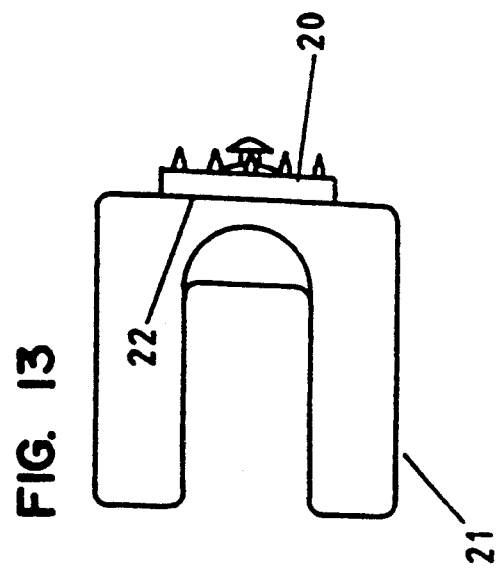

FIGS. 11-13 illustrate orientation of the patellar component 1 in use in relation to the femoral component 21. The cylindrical surface 22 of the femoral component engages the generally flat surface of the patellar component along a line, preventing occurrance of any significant degree of shear. A minor amount of shear caused by friction between the bearing surfaces is insufficient to cause failure of the prosthesis. In contrast FIG. 14 shows a prior art arrangement wherein a convex patellar component engages a concave bearing surface of a femoral component. Lateral displacement of the patellar component gives rise to shear forces, causing strain and possible failure of the stem 23 of the patellar component.

We claim:

1. A patellar component for use in conjunction with a prosthetic knee joint having a femoral component and a tibial component, said patellar component comprising a first member having a flat bearing surface for bearing directly against the femoral component and a second surface which is opposite to said flat bearing surface, a second member having means for fixing said second member to a natural patella, and means for holding said first and second members together at said second surface, so that said flat bearing surface of said first member bears directly against said femoral component.

2. A patellar component according to claim 1 wherein said first member is a plastic material.

3. A patellar component according to claim 2 wherein the plastic material is ultra-high molecular weight polyethylene.

4. A patellar component according to claim 3 wherein the second member is metal.

5. A patellar component according to claim 1 wherein the metal is stainless steel.

6. A patellar component according to claim 5 wherein both first and second members are flat discs, the first member has a recess in said second surface thereof for receiving the the second member at the second surface.

7. A patellar component according to claim 6 wherein said holding means includes that the first and second members each have a central aperture for receiving a central peg which serves to retain said first and second members together.

8. A patellar component according to claim 7 wherein the central peg also includes a fixation device to be driven into a bone of said natural patella.

9. A patellar component according to claim 7, wherein said holding means further comprises means for fixing the second member to said natural patella, said fixing means comprising a series of spikes spaced equally around a circumference of the second member.

10. A patellar component according to claim 9 wherein said spikes are metal.

11. An endoprosthetic assembly of components for use in total knee replacement, the assembly including a femoral component for attachment to a femur, a tibial component for attachment to a tibia and a patellar component for attachment, to a natural patella, said patellar component being formed with a flat bearing surface which bears directly against said femoral component, and the femoral component being formed with a substantially cylindrical bearing counterface, the flat bearing surface of the patellar component bearing directly against the cylindrical surface of the femoral component.

* * * * *